United States Patent
Iwao et al.

(10) Patent No.: US 6,305,622 B1
(45) Date of Patent: Oct. 23, 2001

(54) PROCESS FOR PRODUCING TRIHYDROCARBYL ALUMINUMS

(75) Inventors: Tetsuya Iwao; Tadao Nishida; Kaoru Kawanishi; Seijiro Koga, all of Osaka (JP)

(73) Assignee: Nippon Aluminum Alkyls, Ltd., Tokyo (JP)

( * ) Notice: Subject to any disclaimer, the term of this patent is extended or adjusted under 35 U.S.C. 154(b) by 0 days.

(21) Appl. No.: 09/254,781

(22) PCT Filed: Jul. 17, 1998

(86) PCT No.: PCT/JP98/03217

§ 371 Date: Mar. 8, 1999

§ 102(e) Date: Mar. 8, 1999

(87) PCT Pub. No.: WO99/03862

PCT Pub. Date: Jan. 28, 1999

(30) Foreign Application Priority Data

Jul. 18, 1997 (JP) .................................................. 9-194295
Aug. 8, 1997 (JP) .................................................. 9-215036

(51) Int. Cl.⁷ .................................................. B02C 19/12

(52) U.S. Cl. .................................................. 241/23
(58) Field of Search .................................................. 556/180, 186, 556/187, 189; 420/407; 241/23, 30

(56) References Cited

U.S. PATENT DOCUMENTS 2,744,127 * 5/1956 Ziegler et al. .
4,116,992 * 9/1978 Eidt .

FOREIGN PATENT DOCUMENTS 9-136890 * 11/1995 (JP) .
9-77774 * 3/1997 (JP) .

* cited by examiner

*Primary Examiner*—Mark Rosenbaum
(74) *Attorney, Agent, or Firm*—Knobbe, Martens, Olson & Bear, LLP

(57) ABSTRACT

A trihydrocarbyl aluminum is produced at a high yield by reacting an aluminum-magnesium alloy powder with a halogenated hydrocarbon. Prior to the reaction, the alloy powder is obtained by grinding treatment using a ball mill or a vibration ball mill. The reaction is conducted with agitation in the presence of abrasive particles or is conducted using a homogenizer without abrasive particles.

6 Claims, No Drawings

PROCESS FOR PRODUCING TRIHYDROCARBYL ALUMINUMS

This is a 35 USC §371 application of PCT/JP98/03217.

TECHNICAL FIELD PERTINENT TO THE INVENTION

The present invention relates to a process for producing a trihydrocarbyl aluminum which is an important co-catalyst for olefin polymerization.

PRIOR ART

The process for synthesizing a trialkyl aluminum from an aluminum-magnesium alloy and a halogenated alkyl is known and is described in, for example, U.S. Pat. No. 2,744,127 of K. Ziegler.

In this U.S. Patent use of an aluminum-magnesium alloy composed of 35 to 43% aluminum and 57 to 65% magnesium is described. It is also described that trimethyl aluminum can be synthesized at a yield of 60 to 75% from methyl bromide and the above aluminum-magnesium alloy. The literature, however, makes no mention of whether or not trimethyl aluminum can be synthesized from methyl chloride and an aluminum-magnesium alloy.

It is also described that triethyl aluminum can be synthesized from ethyl bromide and an aluminum-magnesium alloy at a yield of 75 to 85%. The literature gives an Example wherein triethyl aluminum can be synthesized from ethyl chloride and an aluminum-magnesium alloy, but makes no mention on the yield.

In the synthesis of trimethyl aluminum, there has been an industrially and economically serious drawback in that particularly when methyl chloride of low cost and easy availability is used in volume, the reaction does no proceed favorably.

The primary object of the present invention is to provide a process which can produce trimethyl aluminum using methyl chloride of low cost and easy availability in volume, at a yield at least equal to that obtained using iodide or bromide.

Another object of the present invention is to provide a process wherein the reaction proceeds easily and the yield is high when compared with conventional processes, even when an iodinated hydrocarbon or a brominated hydrocarbon is used as a raw material.

MEANS FOR ACHIEVING THE TASK

The present inventors conducted a study in order to solve the above problems and, as a result, have completed the present invention. The present invention comprises the following invention and embodiments.

(1) A process for producing a trihydrocarbyl aluminum by reacting an aluminum-magnesium alloy containing 20 to 80% by weight aluminum and 80 to 20% by weight magnesium, with a halogenated hydrocarbon, in which process
the aluminum-magnesium alloy has been subjected to a grinding treatment in the presence of an abrasive medium by the use of a ball mill or a vibration ball mill, and/or,
in the reaction, agitation is conducted in the presence of an abrasive medium or there is used a homogenizer rotating at a high speed of 5,000 to 20,000 rpm.

(2) A process for producing a trihydrocarbyl aluminum by reacting an aluminum-magnesium alloy with a halogenated hydrocarbon according to the above (1), in which process,
in the reaction, agitation is conducted in the presence of an abrasive medium.

(3) A process for producing a trihydrocarbyl aluminum by reacting an aluminum-magnesium alloy with a halogenated hydrocarbon according to the above (1), in which process,
in the reaction, there is used a homogenizer rotating at a high speed of 5,000 to 20,000 rpm.

(4) A process for producing a trihydrocarbyl aluminum by reacting an aluminum-magnesium alloy with a halogenated hydrocarbon according to the above (1), in which process
the aluminum-magnesium alloy has been subjected to a grinding treatment in the presence of an abrasive medium by the use of a ball mill or vibration ball mill, and
in the reaction, agitation is conducted in the presence of an abrasive medium.

(5) A process for producing a trihydrocarbyl aluminum according to any of the above (1) to (4), wherein the aluminum-magnesium alloy contains 35 to 45% by weight of aluminum and 55 to 65% by weight of magnesium.

(6) A process for producing a trihydrocarbyl aluminum according to any of the above (1) to (5), wherein the halogenated hydrocarbon is used in an amount of 2.0 to 10.0 moles per mole of the aluminum in the aluminum-magnesium alloy.

(7) A process for producing a trihydrocarbyl aluminum according to any of the above (1) to (6), wherein the halogenated hydrocarbon is a methyl halide.

(8) A process for producing a trihydrocarbyl aluminum according to the above (7), wherein the halogenated hydrocarbon is methyl chloride.

MODE FOR CARRYING OUT THE INVENTION

The present invention is hereinafter described in more detail.

The reaction of the present invention is represented by the following reaction formula when the aluminum-magnesium alloy used is $Al_2Mg_3$.

$$Al_2Mg_3 + 6RX \rightarrow 2AlR_3 + 3MgX_2 \qquad (1)$$

In the above formula, R is a chain or cyclic hydrocarbon residue having 1 to 20 carbon atoms, or an aryl group having 6 to 20 carbon atoms, and specific examples thereof are methyl group, ethyl group, n-propyl group, isopropyl group, n-butyl group, isobutyl group, sec-butyl group, n-hexyl group, n-octyl group, cyclohexyl group, phenyl group and benzyl group; X is chlorine, bromine or iodine.

In the present invention, particularly remarkable effects can be obtained when RX is methyl chloride.

In the aluminum-magnesium alloy used in the reaction, the atomic composition is such that the aluminum content is 20 to 80% by weight, preferably 30 to 60% by weight, particularly preferably 35 to 45% by weight and the magnesium content is 80 to 20% by weight, preferably 40 to 70% by weight, particularly preferably 55 to 65% by weight.

There is no particular restriction as to the atomic composition of the aluminum-magnesium alloy as long as the composition is in the above range.

However, an atomic composition consisting of 35 to 45% by weight of aluminum and 55 to 65% by weight magnesium is particularly preferred.

The aluminum-magnesium alloy having the above atomic composition is preferred because the amounts of the two components in the alloy are close to stoichiometric amounts and moreover the alloy is very brittle and can be easily made into a fine powder by the grinding treatment described later. Since the aluminum-magnesium alloy of the above atomic composition, i.e. a composition close to $Al_2Mg_3$ leaves little reside in the reaction and is preferred economically and industrially, the most preferred atomic composition is a composition close to $Al_2Mg_3$ (Al: 42.6% by weight, Mg: 57.4% by weight). When a commercially available alloy is out of this compositional range, magnesium or aluminum is added thereto and, as necessary, grinding is conducted, whereby a particularly preferred compositional range can be obtained.

It is generally known that aluminum-magnesium alloy consists of various kinds of crystals, each of which is different in atomic composition. In order to carry out the reaction smoothly, it is preferable that the aluminum-magnesium alloy used in the present invention be as uniform as possible in crystal structure and atomic composition throughout the alloy portion. Moreover, it is desirable that the crystal structure be as amorphous as possible.

An aluminum-magnesium alloy uniform in crystal structure and in atomic composition throughout the alloy portion, such as mentioned above, can be obtained by melting aluminum and magnesium and then cooling the melt rapidly.

As a method for rapidly cooling the melt of aluminum and magnesium, there can be employed, for example, a well-known method used in production of amorphous alloy, such as the atomization method, liquid rapid cooling method or the like.

The above-mentioned aluminum-magnesium alloy is used in the state of a fine powder. When the fine powder is obtained by a grinding treatment in the presence of an abrasive medium by the use of a ball mill or a vibration ball mill (Vibratom), a good result can be obtained. However, the present invention process is applicable also to a case of using a fine powder of aluminum-magnesium alloy produced by the known atomization or stamp mill method.

Grinding by ball mill is conducted by feeding an abrasive medium (balls) and a material to be ground, into a container and grinding the material to be ground, into a fine powder by collision with moving balls. It is generally carried out by rotating the container by an external force, but may be carried out in other ways.

Grinding by vibration ball mill is a kind of the above mentioned grinding by ball mill, and is conducted by feeding an abrasive medium (balls) and a material to be ground, into a container and vibrating the container vigorously vertically and horizontally by an external force to grind the material to be ground, into a fine powder by collision with moving balls. In the present invention, use of, in particular, a vibration ball mill is recommended in view of the grinding efficiency.

There is no particular restriction as to the kind of the abrasive medium used. However, the abrasive medium can be exemplified by balls made of a metal such as iron, stainless steel or the like; and balls made of a ceramic (e.g. silica or alumina), glass, agate or the like. There is no particular restriction as to the size of the abrasive medium; however, the size is appropriately a sphere of about 0.2 to 3 cm in diameter. The amount of the abrasive medium used can be appropriately determined depending upon the amount of the aluminum-magnesium alloy to be ground; however, it is generally about 2 to 30 times the weight of the aluminum-magnesium alloy used. A very small amount of a grinding aid such as stearic acid or the like may be used to improve the efficiency of grinding.

The grinding time varies depending upon the amount of the material to be ground, the amount and shape of the abrasive material and the operating conditions of the grinding apparatus; however, it is generally about 5 minutes to 96 hours and, when a vibration ball mill is used, is about 5 minutes to 24 hours.

The halogenated hydrocarbon used in the process of the present invention can be one of ordinary availability, but is preferably free from oxygen or water.

The halogenated hydrocarbon used in the present invention is represented by the general formula RX. In the formula, R is a saturated or unsaturated chain or cyclic hydrocarbon residue having 1 to 20 carbon atoms, or an aryl group having 6 to 20 carbon atoms. Specific examples of R are methyl group, ethyl group, n-propyl group, isopropyl group, n-butyl group, isobutyl group, sec-butyl group, n-hexyl group, n-octyl group, cyclohexyl group, phenyl group and benzyl group. X is chlorine, bromine or iodine.

The effects of the present invention are exhibited clearly when the halogenated hydrocarbon is methyl chloride.

The present inventors conducted a study on the reactivity when the above-mentioned aluminum-magnesium alloy was suspended in a reaction solvent in a reaction vessel and, while the suspension was agitated, methyl chloride as halogenated hydrocarbon was added. However, the yield was unexpectedly low.

As a result of a further study, it was found out that when the agitation was conducted in the presence of an abrasive medium, the yield increased to 5 times or more. The finding led to the completion of the present invention.

As the reactor used in the reaction, a vertical or horizontal pressure-resistant reactor is used. For example, an autoclave equipped with an agitator is used. The blade used therein can be any is blade which is generally known, such as propeller, turbine, Pfaudler type, Maxblend type, full zone type or the like. Agitation is conducted in the presence of an abrasive medium, which is a feature of the present invention.

The abrasive medium consists of nearly spherical particles made of a glass, silica, a ceramic (e.g. alumina), agate, a metal (e.g. iron or SUS) or the like. These particles are moved and caused to collide with each other by the agitation of the agitator blades, whereby they can grind the solid contained in the reaction mixture.

The size of the abrasive medium is generally about 0.5 to 10 mm, preferably 2 to 5 mm, in diameter.

The amount of the abrasive medium fed differs depending upon chemical factors such as concentrations and viscosities of reagents contained in reaction mixture, and the like and engineering factors such as size of the reaction vessel, size and shape of the blade, and the like; however, it is preferably 10 to 50% by weight of the total weight of the reaction mixture.

The effects of the abrasive medium of the present invention are described in detail. It is presumed that by conducting agitation in the presence of an abrasive medium in the reaction between aluminum-magnesium alloy and methyl chloride, the magnesium chloride (which is formed as a by-product in the reaction and adheres strongly on the surface of the solid aluminum-magnesium alloy) is rubbed off and the surface is always kept fresh; as a result, the reaction between solid aluminum-magnesium alloy and methyl chloride dissolved in solvent can proceed smoothly without being interrupted by the by-product; thereby, trimethyl aluminum can be obtained stably at a high yield.

It is also presumed that the aluminum-magnesium alloy is ground into a finer state in the course of the reaction by collision with the abrasive medium particles; the surface area of the alloy participating in the reaction becomes larger; thereby, the reaction speed becomes faster; and trimethyl aluminum can be obtained at a higher yield.

In the reaction of the present invention, it is possible to use a homogenizer rotating at a high speed of 5,000 to 20,000 rpm, whereby superior effects can be obtained as compared with the case of a reaction using ordinary agitation.

The above homogenizer is one ordinarily called "homogenizer" in the related field. It is an apparatus for giving rise to agitation and emulsification by the utilization of the impact and eddy current caused by the blades rotating at a high speed. It can use blades rotating at a high speed only, or can combine the blades with stationary blades. It is also possible to use the homogenizer described on page 440 of "Shinpan Kagaku Kogyo Jiten" (published by Maruzen Co.).

In the present process, the speed of agitation employed in the reaction between the aluminum-magnesium alloy and the halogenated hydrocarbon is determined by the size of reaction vessel, the amount of abrasive medium, the amounts of reagents and solvent, etc. However, the agitation speed can ordinarily be 50 to 5,000 rpm.

The amount of halogenated hydrocarbon used can be 2 quivalents or more relative to the aluminum in the aluminum-magnesium alloy. Use of the halogenated hydrocarbon preferably in an amount of 3 equivalents (theoretical amount as seen in the formula (1)) or more, more preferably in an excessive amount relative to aluminum, can give a good yield. Use in an amount of 3.5 equivalents or more, most preferably in an amount of 4 equivalents or more, is recommendable to obtain a high yield. There is no particular restriction as to the upper limit of the amount of the halogenated hydrocarbon; however, use of the halogenated hydrocarbon in an amount of about 10 equivalents relative to aluminum is sufficient.

The reaction is conducted by adding the halogenated hydrocarbon to the aluminum-magnesium alloy. The addition may be continuous or intermittent.

It is also possible to mix beforehand the aluminum-magnesium alloy with part of the halogenated hydrocarbon in a reaction vessel and, after the reaction has been started, add the remainder of the halogenated hydrocarbon. It is also possible to add, as a reaction initiator to shorten the induction period of the reaction and start the reaction quickly, a small amount of an alkyl aluminum halide (e.g. alkyl aluminum sesquichloride, dialkyl aluminum chloride or alkyl aluminum dichloride), iodine, aluminum bromide or the like.

In the reaction, a solvent may be used. As the solvent, there can be mentioned, for example, aromatic hydrocarbons such as benzene, toluene, xylene and the like; and aliphatic hydrocarbons such as hexane, heptane, octane, liquid paraffin and the like.

An ether compound can also be used. However, the ether compound forms a coordination compound with the alkyl aluminum formed and it is difficult to separate the ether compound from the alkyl aluminum.

The reaction is exothermic. When the halogenated hydrocarbon is fed intermittently, agitation is continued from the completion of the feeding to the completion of the reaction. When the halogenated hydrocarbon is fed continuously, the feeding rate is controlled to prevent an excessive temperature increase of the reaction system caused by heat generation.

The reaction temperature is about 20 to 170° C., preferably about 30 to 150° C., particularly preferably about 80 to 125° C. The reaction time is about 1 to 48 hours.

In a preferred embodiment of the present invention, an aluminum-magnesium alloy containing 35 to 45% by weight aluminum and 55 to 65% by weight magnesium is reacted with a halogenated hydrocarbon with agitation to obtain a trihydrocarbyl aluminum, wherein the agitation is conducted in the presence of an abrasive medium (the use of this abrasive medium is a feature of the present invention).

There are conventional processes for obtaining a trialkyl aluminum from an aluminum-magnesium alloy and a halogenated alkyl. However, the process of the present invention for synthesizing a trihydrocarbyl aluminum from an aluminum-magnesium alloy and a halogenated hydrocarbon under particular conditions, has not been known.

The present inventors fount that when an aluminum-magnesium alloy containing 20 to 80% by weight aluminum and 80 to 20% by weight magnesium is reacted with a halogenated hydrocarbon in a solvent with agitation (the agitation is conducted preferably in the presence of an abrasive medium), the reaction speed increases and an intended trihydrocarbyl aluminum can be obtained in a short period of time and at a high yield. The present invention has been completed based on this finding.

After the completion of the reaction, a solid composed mainly of magnesium chloride (a by-product) and unreacted solid reagent are separated from the reaction mixture containing the trihydrocarbyl aluminum formed. The solid-removed reaction mixture is subjected to distillation or simply to solvent removal, whereby a product is recovered. However, this initial product right after the above step contains a slight amount of a chloride; therefore, it is preferable that the initial product be subjected to a dechlorination reaction at a temperature of 80 to 170° C., preferably 80 to 125° C. using a dechlorinating agent such as aluminum-magnesium alloy, metallic magnesium, metallic sodium or the like, to remove the chlorine component from the initial product.

Embodiments

The present invention is described more specifically below by way of Examples. However, the scope of the present invention is not restricted by them.

EXAMPLE 1

Metallic aluminum and metallic magnesium were melt and mixed. The molten mixture was rapidly cooled and solidified to produce an aluminum-magnesium alloy having a composition consisting of 42.4% by weight aluminum and 57.6% by weight magnesium. Subsequently, 200 SUS-made balls each having a diameter of 1.5 cm where charged into an SUS-made cylindrical container having an internal volume of 2 liters. Thereoto was fed 150 g of the above-produced aluminum-magnesium alloy after having been ground to a size of about 2 mm×2 mm. The SUS-made cylindrical container was rotated for about 48 hours to grind the aluminum-magnesium alloy.

Thereafter, the ground aluminum-magnesium alloy was separated from the SUS-made balls and sifted through a screen to collect the portion in the range of 75 to 250 $\mu$m in diameter as an alloy fine powder.

A 2-liter autoclave was equipped with an agitator and a methyl chloride feeder, and the inside of the autoclave was purged with nitrogen. Into the autoclave were fed 45 g of the alloy fine powder obtained by the above grinding treatment using a ball mill (45 g consisted of 0.677 mole of aluminum and 1.099 moles of magnesium) and 170 ml of n-hexane together with 40 g of glass beads of about 3.5 mm in diameter. There was further added methyl aluminum sesquichloride as a reaction initiator. Then, agitation was conducted at room temperature for 3 hours.

Next, methyl chloride was fed into the autoclave while being metered by a transfer pump, to increase the pressure inside the autoclave to 10 kg/cm². Then, while the temperature inside the autoclave was kept at 120° C., 134 g (2.66 moles, 4.0 equivalents relative to aluminum) of methyl chloride was fed to conduct a reaction. The pressure increased from the initial level of 10 kg/cm² to 36 kg/cm².

The time required for the feeding of methyl chloride was 4.2 hours. After the completion of the feeding, the resulting mixture was agitated for further 4 hours. The speed of agitation was 700 rpm during the reaction.

The suspension containing a solid composed mainly of magnesium chloride (a by-product) was filtered to remove the solid to obtain a colorless transparent crude trimethyl aluminum/hexane solution.

The solution was subjected to distillation to remove the hexane to obtain crude trimethyl aluminum as a distillation residue. The crude trimethyl aluminum was quantitatively analyzed for aluminum content and chlorine content.

The aluminum content in the crude trimethyl aluminum, other than that in methyl aluminum sesquichloride was 0.559 mole. This value was 82.6% (crude yield) relative to the aluminum content in the aluminum-magnesium alloy used originally.

The chlorine content in the crude trimethyl aluminum, including that in methyl aluminum sesquichloride was 0.327 mole.

To remove the chlorine content from crude trimethyl aluminum, 20.7 g of the above-mentioned aluminum-magnesium alloy fine powder (20.7 g consisting of 0.325 mole of aluminum and 0.491 mole of magnesium) was added to the crude trimethyl aluminum; and the resulting mixture was agitated in the presence of glass beads of about 3.5 mm in diameter at 120° C. for 24 hours.

The mixture after agitation was analyzed for chlorine content. The chlorine content in the mixture was substantially zero.

Then, the mixture was subjected to distillation to obtain trimethyl aluminum. The yield of trimethyl aluminum was 65.9% relative to the aluminum in the aluminum-magnesium alloy used originally.

EXAMPLE 2

The aluminum-magnesium alloy obtained in the same manner as in Example 1 was ground by using a Vibratom mill (a vibration mill produced by Kawasaki Heavy Industries. Ltd.) in place of the ball mill used in Example 1. The portion in the range of 75 to 250 µm in diameter was separated out and obtained as an alloy fine powder.

The alloy fine powder was subjected to the same reaction as in Example 1 to obtain crude trimethyl aluminum at a yield of 84.5%. The crude trimethyl aluminum was subjected to distillation to obtain trimethyl aluminum at a yield of 67.9%.

EXAMPLE 3

A reaction was conducted in the same manner as in Example 1 except that the amount of methyl chloride used was increased to 4.5 equivalents relative to aluminum, whereby crude trimethyl aluminum was obtained at a yield (crude yield) of 88.5% and, after distillation, trimethyl aluminum was obtained at a yield of 70.3%.

EXAMPLE 4

A reaction was conducted in the same manner as in Example 2 except that the amount of methyl chloride used was increased to 4.5 equivalents relative to aluminum, whereby crude trimethyl aluminum was obtained at a yield (crude yield) of 90.1% and, after distillation, trimethyl aluminum was obtained at a yield of 72.1%.

EXAMPLE 5

A reaction was conducted in the same manner as in Example 1 except that the amount of methyl chloride used was increased to 3.5 equivalents relative to aluminum.

Crude trimethyl aluminum was obtained in the same manner as in Example 1.

The aluminum content in crude trimethyl aluminum, other than that in methyl aluminum sesquichloride was 0.494 mole. This value was 73.0% (crude yield) relative to the aluminum content in the aluminum-magnesium alloy used originally.

The crude trimethyl aluminum was subjected to a dechlorination reaction using aluminum-magnesium alloy, in the same manner as in Example 1. To remove a very small amount of chlorine still remaining in the reaction mixture, metallic sodium in an amount in excess of the chlorine was added to the reaction mixture, and a reaction was allowed to take place to remove the chlorine in the liquid layer. The resulting reaction mixture was subjected to distillation to remove n-hexane. The distillation residue was subjected to distillation to obtain trime5thyl aluminum. The yield thereof was 56% relative to the aluminum in the aluminum-magnesium alloy used originally.

Comparative Example 1

A molten aluminum-magnesium alloy was sprayed in a nitrogen atmosphere by the use of spray dryer, to form fine particles, and the fine particles were collected using a cooled filter to produce an aluminum-magnesium alloy fine powder having the same composition as in Example 1, consisting of 42.4% by weight aluminum and 57.6% by weight magnesium. The fine powder was sieved through a screen to obtain the portion in the range of 75 to 250 µm in particle diameter.

The above-obtained alloy was subjected to a reaction with methyl chloride in the same manner as in Example 1, with the exception that only ordinary agitation was conducted in the reaction; no glass beads were added. Glass beads were used only in the removal of chlorine present in the obtained trimethyl aluminum.

In the above reaction between aluminum-magnesium alloy [45 g (0.677 mole as aluminum)] and methyl chloride [134 g (2.66 moles, 4.0 equivalents relative to aluminum)], the after-purification yield of trimethyl aluminum was 15% (relative to aluminum).

EXAMPLE 6

A reaction was conducted in the same manner as in Example 1, using the same aluminum-magnesium alloy as used in Example 1 with the exception that, in the reaction of the alloy with methyl chloride, only ordinary agitation was conducted without glass beads. Glass beads were used only in the removal of chlorine present in formed trimethyl aluminum.

In the above reaction between aluminum-magnesium alloy [45 g (0.677 mole as aluminum)] and methyl chloride [134 g (2.66 moles, 4.0 equivalents relative to aluminum)], the after-purification yield of trimethyl aluminum was 40% (relative to aluminum).

EXAMPLE 7

Using an aluminum-magnesium alloy obtained in the same manner as in Comparative Example 1 by spraying a molten aluminum-magnesium alloy in a nitrogen atmosphere by the use of a spray dryer, a reaction of the alloy with methyl chloride was conducted in the same manner as in Example 1.

In the above reaction between aluminum-magnesium alloy [45 g (0.677 mole as aluminum)] and methyl chloride [134 g (2.66 moles, 4.0 equivalents relative to aluminum)], the after-purification yield of trimethyl aluminum was 25% (relative to aluminum).

EFFECTS OF THE INVENTION

The process of the present invention has made it possible to synthesize a trihydrocarbyl aluminum at a high yield from an aluminum-magnesium alloy and a halogenated hydrocarbon.

As a result, it has become possible to produce, in particular, trimethyl aluminum, at a far lower cost than before and in high volume.

What is claimed is:

1. A process for producing a trihydrocarbyl aluminum, comprising the steps of:

mixing and melting aluminum and magnesium to obtain an aluminum-magnesium alloy of 20–80% aluminum and 20–80% magnesium;

cooling the alloy to solidify the same;

grinding the alloy to obtain an alloy powder;

reacting the alloy powder with a halogenated hydrocarbon while agitating the alloy powder and the halogenated hydrocarbon, to form a trihydrocarbyl aluminum, wherein the alloy powder and the halogenated hydrocarbon are agitated with abrasive particles or are treated by a homogenizer without abrasive particles; and recovering the trihydrocarbyl aluminum.

2. The process according to claim 1, wherein, in the reaction step, the agitation is conducted at an agitation speed of 50–5,000 r.p.m. or the homogenizer treatment is conducted at a rotation speed of 5,000–20,000 r.p.m.

3. The process according to claim 1, wherein, in the grinding step, the grinding treatment is conducted with abrasive particles.

4. The process according to claim 1, wherein the halogenated hydrocarbon is methyl halide or methyl chloride.

5. In a process for producing a trihydrocarbyl aluminum by reacting an aluminum-magnesium alloy of 20–80% aluminum and 20–80% magnesium with a halogenated hydrocarbon, wherein the improvement comprises agitating with abrasive particles or treating by a homogenizer without abrasive particles the aluminum-magnesium alloy and the halogenated hydrocarbon during the reaction.

6. The improvement according to claim 5, wherein the agitation is conducted at an agitation speed of 50–5,000 r.p.m. or the homogenizer treatment is conducted at a rotation speed of 5,000–20,000 r.p.m.

* * * * *